United States Patent [19]

Sugasawa et al.

[11] Patent Number: 4,560,684

[45] Date of Patent: Dec. 24, 1985

[54] 1,4-BENZODIAZEPINE DERIVATIVES

[75] Inventors: Tsutomu Sugasawa, Hyogo; Makoto Adachi; Kazuyuki Sasakura, both of Nara; Akira Matsushita, Hyogo; Masami Eigyo, Nara, all of Japan

[73] Assignee: Shionogi & Co., Ltd., Osaka, Japan

[21] Appl. No.: 560,994

[22] Filed: Dec. 13, 1983

[30] Foreign Application Priority Data

Dec. 21, 1982 [JP] Japan ................... 57-225273

[51] Int. Cl.$^4$ .................. A61K 31/55; C07D 401/04; C07D 403/04
[52] U.S. Cl. ................... 514/221; 260/239.30; 546/201; 546/224; 548/557; 548/447
[58] Field of Search ............... 260/239.3 D; 424/244; 514/229

[56] References Cited

U.S. PATENT DOCUMENTS 3,299,035 1/1967 Archer et al. ............... 260/239.3 D

FOREIGN PATENT DOCUMENTS 2010836 2/1970 France .................. 260/239.3 D
1253370 11/1971 United Kingdom ........ 260/239.3 D

OTHER PUBLICATIONS

Archer and Sternbach, "Chem. Reviews", vol. 68, No. 6, (1968) pp. 747–782.

Primary Examiner—Robert T. Bond
Attorney, Agent, or Firm—Wenderoth, Lind & Ponack

[57] ABSTRACT 1,4-Benzodiazepine derivatives of the formula:

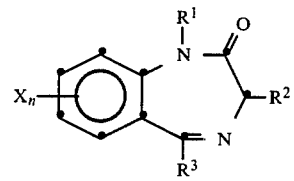

(in which
$R^1$ is pyrrolidinyl or piperidinyl each optionally substituted by $C_{1-3}$ alkyl, phenyl-$C_{1-3}$ alkyl, $C_{1-5}$ alkanoyl, or $C_{2-5}$ alkoxycarbonyl,
$R^2$ is hydrogen, hydroxy, or acetoxy,
$R^3$ is $C_{1-3}$ alkyl, phenyl-$C_{1-3}$ alkyl, or phenyl optionally substituted by one or two halogens,
X is hydrogen, halogen, $C_{1-3}$ alkyl, $C_{1-3}$ alkoxy, nitro, trifluoromethyl, or di-$C_{1-3}$ alkyl-amino, and
n is 1 or 2)

or pharmaceutically acceptable acid addition salts thereof, which are useful as a psychotropic agent such as anti-depressant or anxiolytic agent can be prepared from several routes.

15 Claims, No Drawings

1,4-BENZODIAZEPINE DERIVATIVES

The present invention relates to 1,4-benzodiazepine derivatives of the formula:

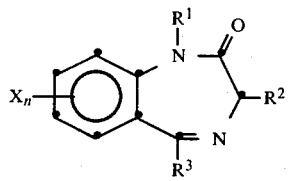

(in which $R^1$ is pyrrolidinyl or piperidinyl each optionally substituted by $C_{1-3}$ alkyl, phenyl-$C_{1-3}$ alkyl, $C_{1-5}$ alkanoyl, or $C_{2-5}$ alkoxycarbonyl, $R^2$ is hydrogen, hydroxy, or acetoxy, $R^3$ is $C_{1-3}$ alkyl, phenyl-$C_{1-3}$ alkyl, or phenyl optionally substituted by one or two halogens, X is hydrogen, halogen, $C_{1-3}$ alkyl, $C_{1-3}$ alkoxy, nitro, trifluoromethyl, or di-$C_{1-3}$ alkyl-amino, and n is 1 or 2)

or pharmaceutically acceptable acid addition salts thereof, which are useful as antidepressants or anxiolytic agents.

Concrete examples of the terms used in the specification are illustratively shown below:

$C_{1-3}$ alkyl refers to methyl, ethyl, propyl, and isopropyl, $C_{1-3}$ alkoxy refers to methoxy, ethoxy, propoxy, and isopropoxy, di-$C_{1-3}$ alkyl-amino refers to dimethylamino, diethylamino, dipropylamino, methylethylamino, methylpropylamino, and ethylpropylamino, phenyl-$C_{1-3}$ alkyl refers to benzyl, phenethyl, and phenylpropyl, $C_{1-5}$ alkanoyl refers to formyl, acetyl, propionyl, isopropionyl, butyryl, isobutyryl, pivaloyl, valeryl, or isovaleryl, $C_{2-5}$ alkoxycarbonyl refers to methoxycarbonyl, ethoxycarbonyl, propoxycarbonyl, butoxycarbonyl, isobutoxycarbonyl, or t-butoxycarbonyl, amino-protecting group refers to those ordinarily used in the peptide chemistry such as benzyloxycarbonyl, trityl, or t-butoxycarbonyl, and halogen refers to fluorine, chlorine, bromine, or iodine.

The pharmaceutically acceptable acid addition salts of the objective compounds (I) illustratively include salts of an inorganic acid such as sulfuric acid, hydrochloric acid, hydrobromic acid, nitric acid or phosphoric acid and those of an organic acid such as acetic acid, citric acid, maleic acid, malic acid, succinic acid, tartaric acid, cinnamic acid, benzoic acid or methanesulfonic acid.

The objective compounds (I) can be prepared in accordance with the reaction scheme as shown below:

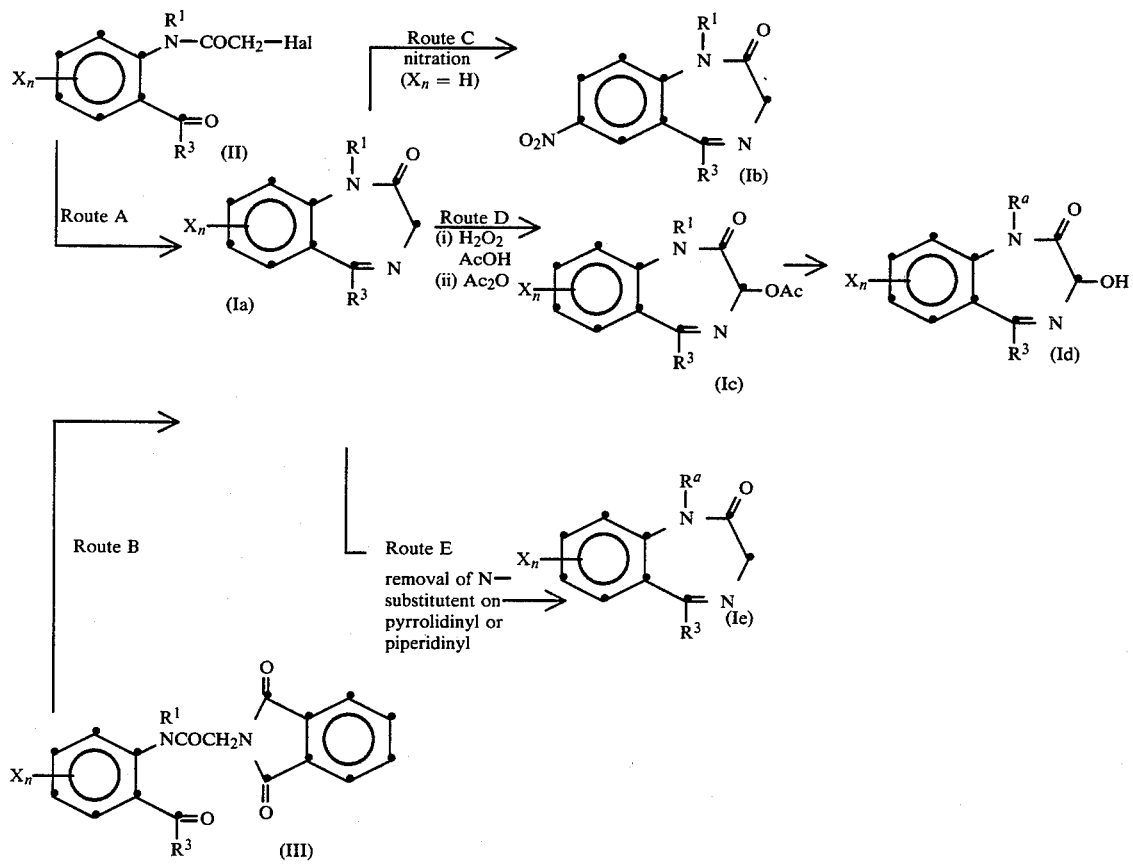

(in which Ac is acetyl, Hal is halogen, $R^a$ is pyrrolidinyl or piperidinyl, $R^1$ is pyrrolidinyl or piperidinyl each optionally substituted by alkyl, phenylalkyl, alkanoyl, alkoxycarbonyl or amino-protecting group, and $R^3$, X, and n each is as defined above)

Route A

The objective compound (Ia) may be prepared by reacting the starting material (II) with an ammoniac reagent such as ammonia or ammonium carbonate. This reaction is performed in the range of temperature from about 15° to 150° C., preferably 40° to 90° C. in an appropriate solvent such as acetonitrile, dimethylformamide, hexamethylphosphoric triamide, tetrahydrofuran, acetone, or methanol. For accelerating the reaction rate, the starting material (II) may be previously reacted with an alkali halide containing other more reactive halogen (e.g. potassium iodide, sodium iodide, lithium iodide, etc.) to lead another more reactive halo-acetyl compound (IIa).

Further the starting material (II) may be prepared by reacting the corresponding anilino compound (IV) HCl with a haloacetyl halide (V) (e.g. chloroacetyl chloride, bromoacetyl bromide, or the like). If necessary, an organic base or inorganic base may be added as an appropriate acid-removing agent.

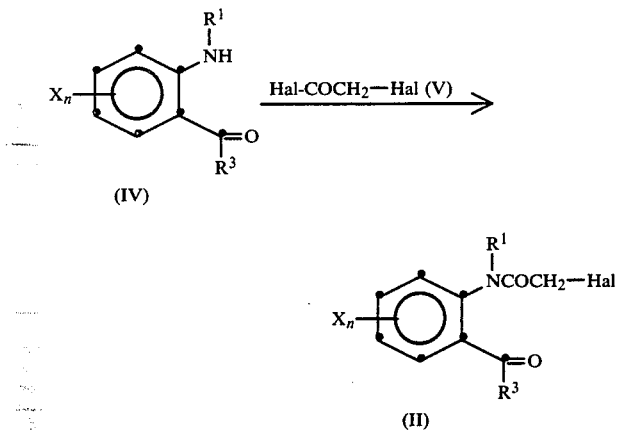

(in which $R^3$, Hal, X, and n are as defined above, and $R^1$ is pyrrolidinyl or piperidinyl each optionally substituted by $C_{1-3}$ alkyl, phenyl-$C_{1-3}$ alkyl, $C_{1-5}$ alkanoyl, $C_{2-5}$ alkoxycarbonyl, or amino-protecting group).

Route B

The objective compound (Ia) may be prepared by reacting the starting material (III) with hydrazine or hydrazine hydrate. The present reaction is performed in the range of temperature from about 30° to 160° C. preferably 45° to 100° C. in an appropriate solvent such as methanol, ethanol, chloroform, benzene, dimethylsulfoxide, or dimethylformamide according to the Gabriel synthesis. This reaction has an advantage that the reaction time is comparatively shorter but a disadvantage that the Smile rearrangement would eventually take place partially as a side reaction.

The starting material (III) may be, for example, prepared by reacting an anilino compound (IV) with a phthaloylglycyl halide (VI) in the presence of an organic or inorganic base such as triethylamine, pyridine, sodium hydride, potassium carbonate, sodium hydrogen-carbonate, or potassium methoxide. The reaction is performed in an appropriate solvent in the range of temperature from room temperature to temperature under heating, for example, about 15° to 100° C.

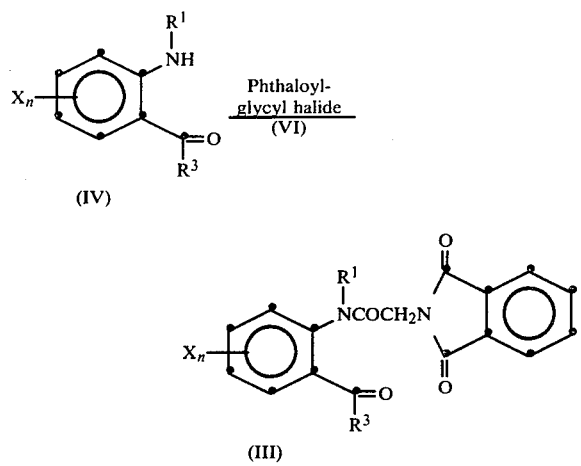

(in which $R^1$ is as given in Route A, and $R^3$, Hal, X and n are as given earlier).

Route C

Benzodiazepine (Ia)($X_n$=H) is nitrated to afford the corresponding 7-nitro compound (Ib). The nitration is performed under cooling at about $-30°$ C. to 0° C. using a customary nitrating agent such as conc. sulfuric acid-nitric acid mixture or conc. sulfuric acid-potassium nitrate mixture.

Route D

3-Hydroxybenzodiazepines (Id) can be prepared in a conventional manner, for example, by oxidizing the starting material (Ia)($R^1$=N-protected pyrrolidinyl or piperidinyl) for N-oxidation, heating the resulting N-oxide with acetic anhydride for rearrangement to afford once the O-acetate (Ic) and hydrolyzing the acetoxy group in a solvent at temperature of about 15° to 120° C. eventually together with deprotection of the amino protecting group. It is sufficient therefor to perform the reaction at about room temperature (e.g. 15° to 25° C.) in the aluminum chloride-anisole-nitromethane-methylene chloride system.

Route E

The 1-piperidinyl- or 1-pyrrolidinyl-benzodiazepines (Ie) can be prepared by subjecting the starting material (Ia)($R^1$=pyrrolidinyl or piperidinyl each substituted by alkyl, preferably methyl, alkoxycarbonyl or amino-protecting group) to removal of the N-substituent on the pyrrolidinyl or piperidinyl in a conventional manner such as in a solvent at temperature of about 15° to 150° C. For example, deprotection of benzyloxycarbonyl may be performed, using a strong acid such as hydrogen bromide-acetic acid mixture, trifluoroacetic acid or catalytic hydrogenation in addition to the aluminum chloride, anisole-nitromethane-methylene chloride system as described in Route D. Removal of trityl group can be attained by treating with dilute acetic acid or the like acids. Dealkylation, in particular demethylation may be attained in a conventional manner by the methods already known, for example, by reacting an N-methyl compound with ethyl chlorocarbonate in the presence of diisopropylethylamine in a solvent such as benzene or toluene under refluxing and then heating the resulting N-ethoxycarbonyl compound under mild conditions with e.g. dialkyl sulfide and methanesulfonic acid.

The starting material (IVa) can be prepared through the following synthetic route:

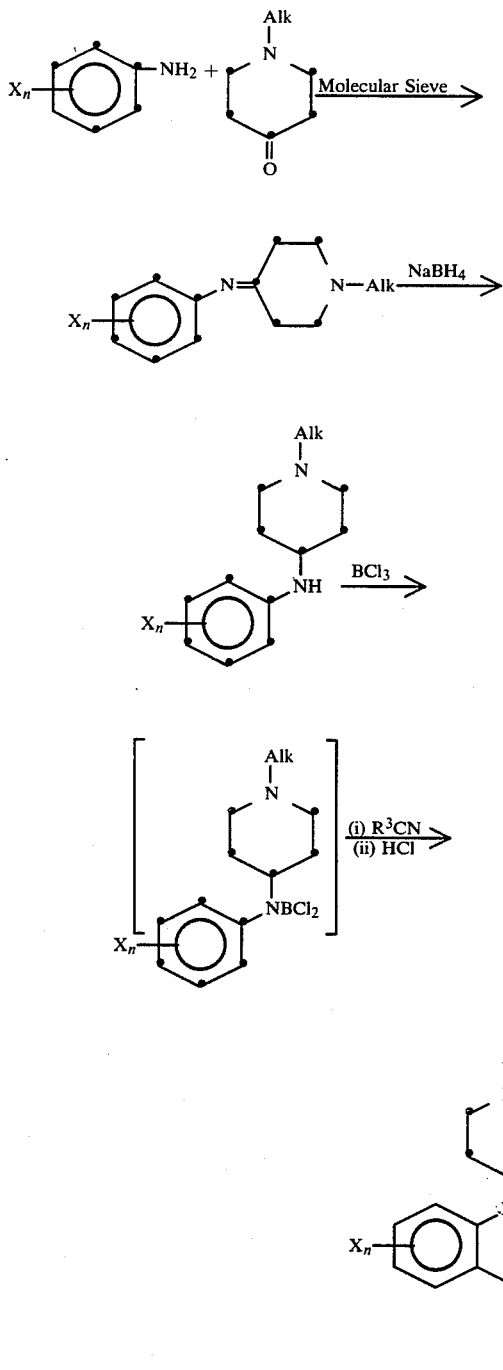

[Sugasawa et al., J.Am.Chem.Soc., 100, 4842 (1978)].

A preferred compound of the products (I) fallen in the scope of the present invention is shown by the formula:

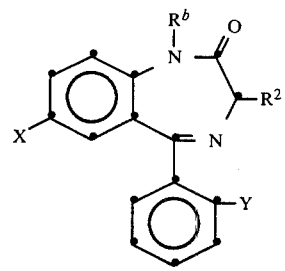

(in which $R^b$ is 3-pyrrolidinyl or 4-piperidinyl each optionally substituted by $C_{1-3}$ alkyl, phenyl-$C_{1-3}$ alkyl, $C_{1-5}$ alkanoyl, or $C_{2-5}$ alkoxycarbonyl, $R^2$ is hydrogen or hydroxy, and X and Y each is hydrogen or halogen).

The objective compound (I) or its pharmaceutically acceptable acid addition salt is useful as a psychotropic agent such as antidepressant or anxiolytic agent. Results of the pharmacological experiments are below shown. Compound No. used in the following table corresponds to the number of Example, in which the same compound has been prepared.

| Compound No. | Acute Toxicity* (mg/kg, presumed) | Anti-TBZ ptosis** ($ED_{50}$, mg/kg) | Anti-PTZ*** convulsion ($ED_{50}$, mg/kg) |
| --- | --- | --- | --- |
| 6 | >200 | 0.26 | >20 |
| 8 | 100–200 | 0.205 | >10 |
| 10 | >200 | 1.3 | 0.77 |
| 15 | >200 | 0.839 | >10 |
| 23 | >200 | 0.075 | 8.52 |
| 26 | >200 | 0.063 | >10 |
| imipramine | >200 | 0.799 | >10 |

Note:
Each compound was used in the form of 0.5 to 1% suspension made by mixing with its half volume of arabic gum.
*Acute toxicity test: To DS male mice in 4 to 5 weeks age was subcutaneously administered 100 to 200 mg of the test compound, and the number of dead mice was measured over a period of seven days. Result was shown by a presumed $LD_{50}$ (mg/kg).
**Antagonism to the tetrabenazine (TBZ) induced ptosis: To several groups of DS male mice in 4 to 5 weeks age, each group consisting of 5 mice was subcutaneously administered the test compound. Half an hour later, 50 mg/kg of tetrabenazine was subcutaneously administered. Degree of the ptosis in 1 hour was scored, and the result was subjected to the rigid conversion. The $ED_{50}$ value was obtained from the regression straight-line.
***Antagonism to the pentylenetetrazole (PTZ) induced convulsion: To several groups of ddy male mice in 4 to 5 weeks age, each group consisting of 8 mice was orally administered the test compound. Half an hour later, 125 mg/kg of pentylenetetrazole was subcutaneously administered, and the number of mice surviving during 2 hours was observed. The $ED_{50}$ value was obtained from the survival number according to the probit method.

The objective compounds (I) or their pharmaceutically acceptable acid addition salts may be administered singly or together with appropriate carriers, diluents, and/or excipients such as wheat starch, corn starch, potato starch or gelatin. The choice of a carrier, diluent, and/or excipient will be decided, depending upon the preferred route of administration, solubility of the compound used as an effective ingredient, and pharmaceutical standard practice. Exemplary preparations are tablets, capsules, pills, suspensions, syrups, powders, solutions, suppositories, and these preparations may be formulated in a conventional manner. Daily oral dosage of the objective compound (I) or its pharmaceutically acceptable salt ot adult humans when available as an antidepressant or anxiolytic agent is about 0.1 to 300 mg.

Presently preferred and practical embodiments of the present invention are illustratively shown in the following examples and referential examples.

EXAMPLE 1

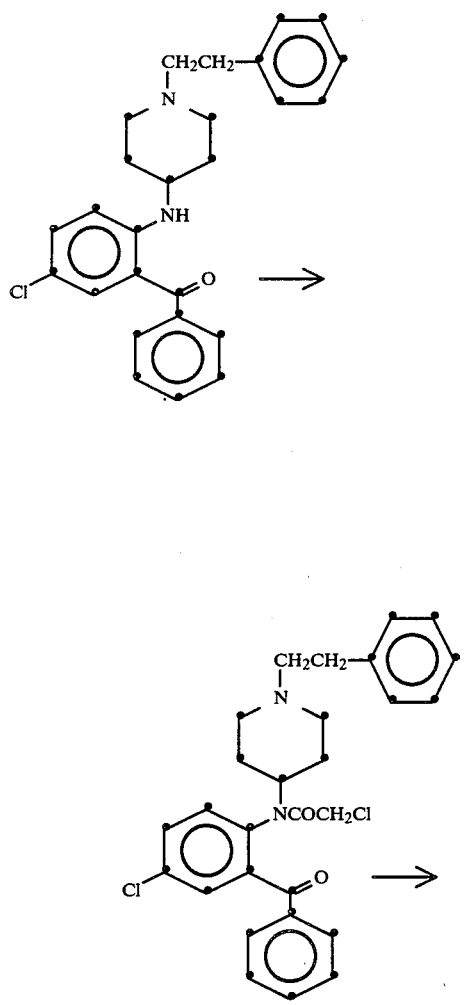

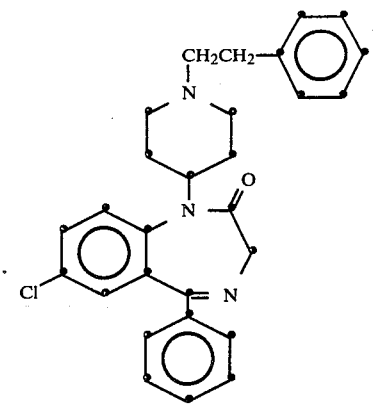

A mixture of 4-(4-chloro-2-benzoylanilino)-1-phenethylpiperidine hydrochloride (2.85 g, 5.9 mmol) and 2-chloroacetyl chloride (0.94 ml, 5.9×2 mmol) in acetonitrile (20 ml) is refluxed under heating over a period of 1 hour, and the reaction mixture is concentrated in vacuo. The residue is mixed with sodium iodide (2.6 g, 5.8×3 mmol) and acetonitrile (50 ml), and the resultant mixture is stirred at 70° C. (bath temp.) over a period of 2.5 hours. After cooling, the reaction mixture is mixed with ammonium carbonate (6 g) and stirred at room temperature over a period of 10 days. The reaction mixture is concentrated in vacuo, and the residue is mixed with water and extracted with methylene chloride. The methylene chloride layer is washed with water, dried over anhydrous potassium carbonate and concentrated in vacuo. The residue is chromatographed on a column of alumina, which is eluted with benzene containing 5% ethyl acetate. The eluate is concentrated in vacuo to give an oil (2.28 g), which is again purified by the same chromatography as above to give 7-chloro-1,3-dihydro-1-(1-phenethyl-4-piperidinyl)-5-phenyl-2H-1,4-benzodiazepin-2-one (1.75 g) as an oil. The yield is 67%. The oxalate, mp. 217°–219° C. dec. (ethanol).

Intermediary chloroacetamide hydrochloride, mp. 235°–238° C. (dec.).

EXAMPLES 2-4

The reactions are performed as in Example 1, whereby the following intermediate (IIa) and objective compound (If) are prepared.

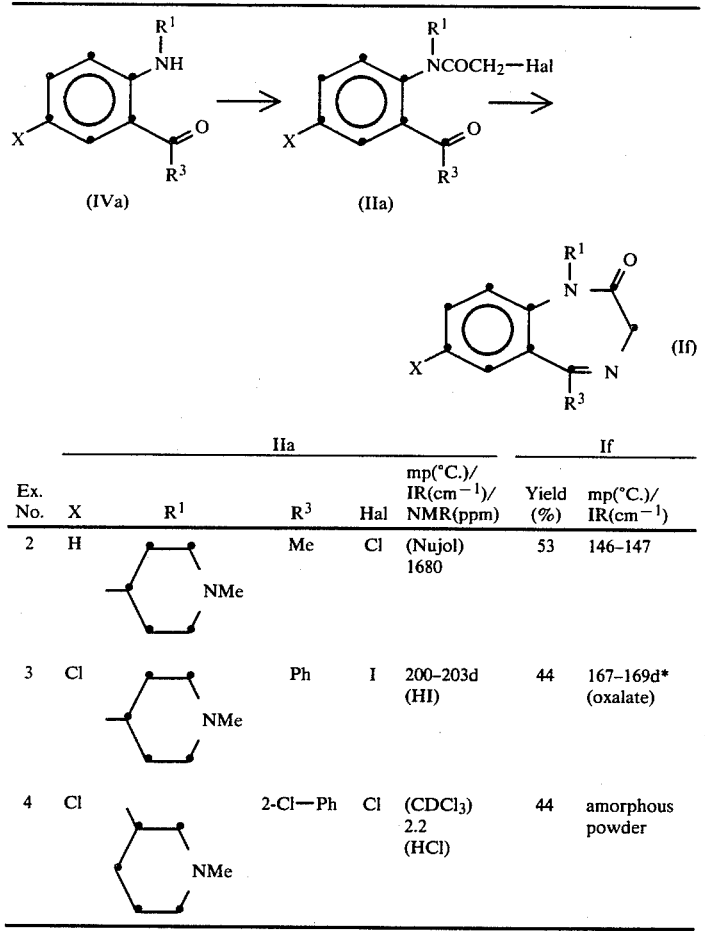

| Ex. No. | X | R¹ | R³ | Hal | IIa mp(°C.)/ IR(cm⁻¹)/ NMR(ppm) | Yield (%) | If mp(°C.)/ IR(cm⁻¹) |
|---|---|---|---|---|---|---|---|
| 2 | H | (piperidine-NMe) | Me | Cl | (Nujol) 1680 | 53 | 146–147 |
| 3 | Cl | (piperidine-NMe) | Ph | I | 200–203d (HI) | 44 | 167–169d* (oxalate) |
| 4 | Cl | (piperidine-NMe) | 2-Cl—Ph | Cl | (CDCl₃) 2.2 (HCl) | 44 | amorphous powder |

Note: Me (methyl), Ph (phenyl), d (decomposition).
*The hydrochloride: mp. 242-247dec.

EXAMPLE 5

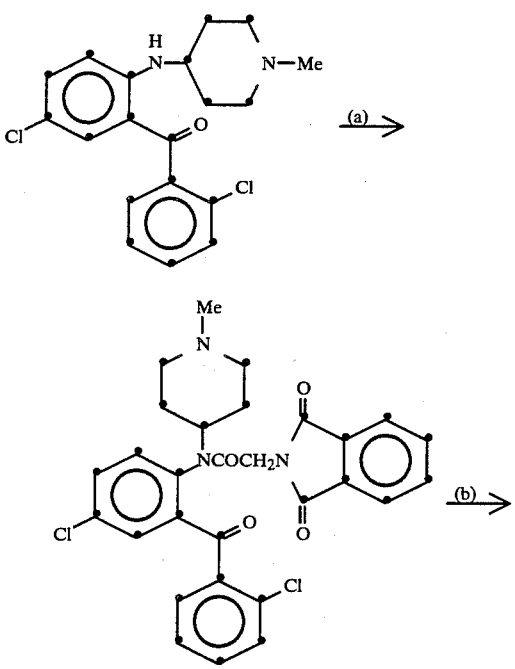

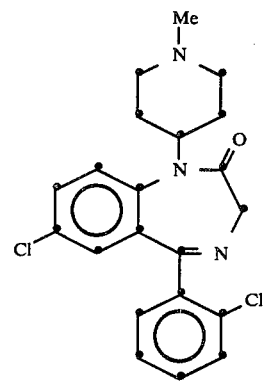

(a) A mixture of 4-[2-(2-chlorobenzoyl)-4-chloroamilino]-1-methylpiperidine (1.5 g, 4.13 mmol) and phthaloylglycyl chloride (1.85 g, 4.13×2 mmol) in acetonitrile (20 ml) is refluxed over a period of 48 hours, and the reaction mixture is concentrated in vacuo. The residue is mixed with ice-2N sodium hydroxide mixture and benzene, and the resultant mixture is stirred at room temperature over a period of half an hour. The benzene layer is separated, and the aqueous layer is extracted with benzene. The benzene layers are combined, washed with water, dried over anhydrous potassium carbonate, and concentrated in vacuo. The residue is chromatographed on a column of alumina, which is eluted with benzene and methylene chloride. The latter part of the benzene eluate and the methylene chloride eluate are combined and concentrated in vacuo and crystallized from methylene chloride-acetone to give N-[4-chloro-2-(2-chlorobenzoyl)phenyl]-N-[4-(1-methylpiperidinyl)]phthaloylglycinamide (926 mg) as crystals melting at 215° to 216° C. The yield is 65%.

(b) A mixture of said product (1.47 g, 2.67 mmol) and 80% hydrazine hydrate (0.39 ml, 2.67×3 mmol) in 95% ethanol is refluxed over a period of half an hour. After cooling, the reaction mixture is mixed with benzene, and the precipitated crystals are filtered off. The filtrate is concentrated in vacuo, and the residue is chromatographed on a column of alumina, which is eluted with benzene and benzene-ethylacetate (1:1) mixture. The eluates are combined and concentrated in vacuo, and the residue is crystallized from ether to give 7-chloro-5-(2-chlorophenyl)-1,3-dihydro-1-(1-methyl-4-piperidinyl)-2H-1,4-benzodiazepin-2-one (694 mg) as crystals melting at 146° to 147° C. The yield is 65%.

EXAMPLES 6-22

The reactions are performed as in Example 5, whereby the following intermediates (III) and the objective compounds (Ia) are perpared.

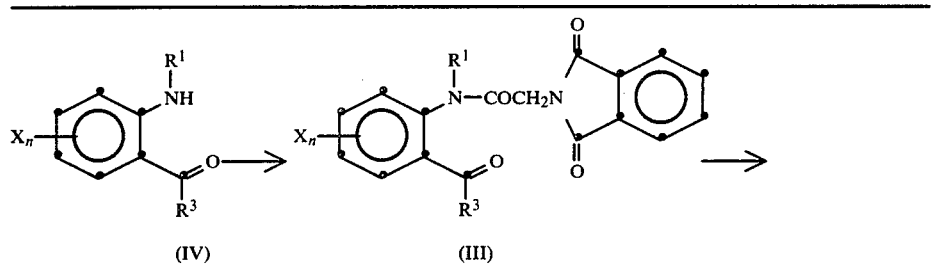

(IV)   (III)

(Ia)

| Ex. No. | III |  |  |  | Ia |  |  |
|---|---|---|---|---|---|---|---|
|  | $X_n$ | $R^1$ | $R^3$ | mp (°C.)/ IR (cm$^{-1}$) | $X_n$ | Yield | mp (°C.)/ IR (cm$^{-1}$) |
| 6 | H | ⌬NMe | Ph | 1770 1720(Nujol) 1660 | H | 59 | 157-159 |
| 7 | 4-MeO | " | 2-F—Ph | 1770 1720(CHCl$_3$) 1630 | 7-MeO | 68 | 76-77 |
| 8 | H | " | " | 194-195 | H | 48 | 123-125 |
| 9 | " | " | 4-F—Ph | 1770 1720(Nujol) 1660 | " | 80 | 1675(CHCl$_3$) |
| 10 | 4-Cl | " | 2-F—Ph | 1775 1720(CHCl$_3$) 1675 | 7-Cl | 72 | 147-149 198-200 (HCl.H$_2$O) |
| 11 | 5-CF$_3$ | " | " | 256-258 | 8-CF$_3$ | 41 | 121-122 |
| 12 | 5-Cl | " | " | 253-254 | 8-Cl | 22 | 203-205d |
| 13 | 5-F | " | " | 229-230 | 8-F | 60 | 200-201 |
| 14 | 4-Br | " | " | 141-143 | 7-Br | 42 | 170-171 |
| 15 | 4-Me | " | " | 1665 1710(Nujol) 1655 | 7-Me | 59 | 139-141 |
| 16 | 4-F | " | " | 182-183 | 7-F | 61 | 146-147 |
| 17 | 4,5-di-Cl | " | " | 228-229 | 7,8-di-Cl | 28 | 168-169 |
| 18 | 4-Me$_2$N | " | " | 200-202 | 7-Me$_2$N | 58 | 142-144 |
| 19 | 6-Cl | " | " | 228-230 | 9-Cl | 14 | 181-182 |
| 20 | 4-Cl | " | 3-Cl—Ph | 130-133d | 7-Cl | 71 | 172-173 |
| 21 | H | " | 2-Br-C$_6$H$_4$-CH$_2$— | amorphous powder | H | 62 | 230-234d (fumarate) |

-continued
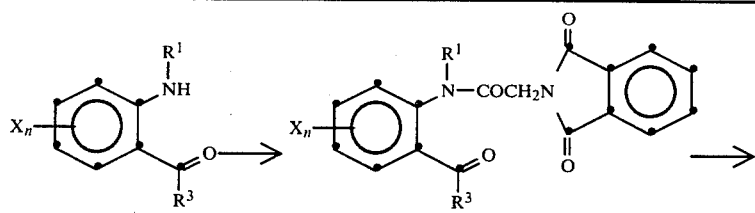
(IV) → (III) →
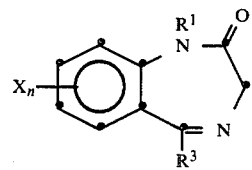
(Ia)
| Ex. No. | III | | | mp (°C.)/ IR (cm$^{-1}$) | Ia | | mp (°C.)/ IR (cm$^{-1}$) |
|---|---|---|---|---|---|---|---|
| | $X_n$ | $R^1$ | $R^3$ | | $X_n$ | Yield | |
| 22 | 4-Cl | —N—Me | 2-Cl—Ph | 1780 1730(CHCl$_3$) 1680 | 7-Cl | 20 | 141–143 |
*NMR, $\delta_{ppm}^{CDCl_3}$: 2.2(s, 3H), 3.97, 4.30(q, J = 16Hz, 2H), 4.43(d, 2H)
Note: MeO(methoxy)
EXAMPLE 23
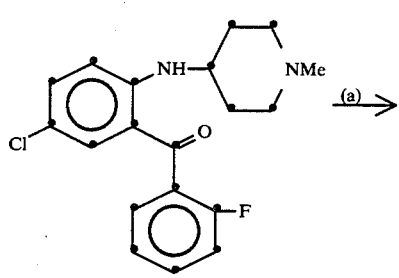 (a)→
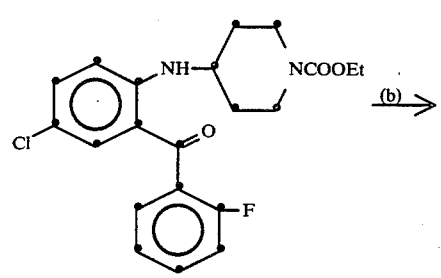 (b)→
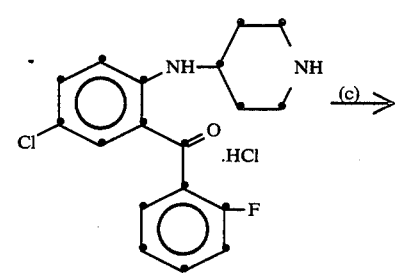 (c)→
-continued
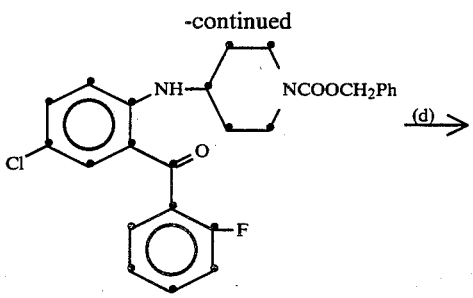 (d)→
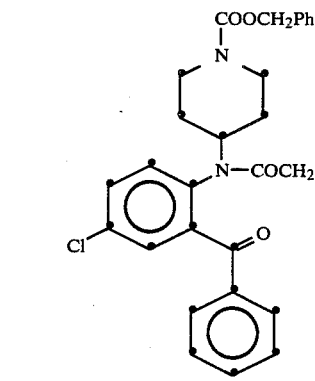 (e)→

-continued

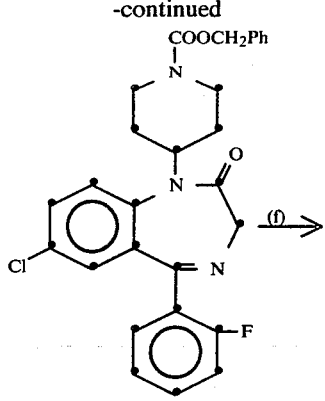

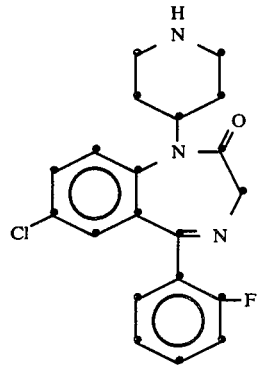

(a) A mixture of 4-[4-chloro-2-(2-fluoro-benzoyl)anilino]-1-methylpiperidine (5.21 g, 15 mmol), ethyl chlorocarbonate (4.30 ml, 15×3 mmol) and diisopropylethylamine (2.61 ml, 15 mmol) in benzene (50 ml) is refluxed over a period of 1 hour. After cooling, the reaction mixture is mixed with icy waters, and the benzene layer is separated, washed with water, dried over anhydrous magnesium sulfate and concentrated in vacuo to give a crystalline residue (6.35 g). The substance is recrystallized from ether-petroleum ether to give 4-[4-chloro-2-(2-fluoro-benzoyl)anilino]-1-ethoxycarbonylpiperidine as crystals melting at 112° to 114° C.

(b) A mixture of said product (6.35 g) obtained in Step (a) and conc.hydrochloric acid-water (1:1) mixture (50 ml) is refluxed over a period of 20 hours. The reaction mixture is concentrated in vacuo to give 4-[4-chloro-2-(2-fluorobenzoyl)anilino]piperidine hydrochloride (5.51 g) as crystals melting at 225° to 228° C.

(c) To a suspension of above product (5.51 g) in a mixture of dioxane (50 ml) and 2N sodium hydroxide (19 ml) is dropwise added a solution of benzyl chlorocarbonate (4 ml, 12.7×2.2 mmol) in dioxane (10 ml) with ice-cooling and stirring, and the resultant mixture is stirred at room temperature over a period of half an hour. Water is added to the reaction mixture, and the mixture is shaken with benzene. The benzene layer is washed with water, dried over anhydrous magnesium sulfate and concentrated in vacuo. The residue (7.74 g) is purified on Lobar ® column B, which is eluted with ethyl acetate-methylene chloride (1:10 v/v). The eluate is concentrated in vacuo to afford 4-[4-chloro-2-(2-fluorobenzoyl)anilino]-1-benzyloxycarbonylpiperidine (5.93 g) as an oil.

IR, $\nu_{max}^{CHCl_3}$, 3330 (NH), 1690, 1625 (CO) cm$^{-1}$ (d) A mixture of above product (5.93 g, 12.7 m mol) obtained in Step (c) and 2-chloroacetyl chloride (2.0 ml, 12.7×2 m mol) in benzene (50 ml) is refluxed over a period of 20 hours. The reaction mixture is concentrated in vacuo to give 4-[N-chloroacetyl-4-chloro-2-(2-fluorobenzoyl)anilino]-1-benzyloxycarbonylpiperidine (6.9 g) as colorless powders.

$^1$H NMR, $\delta_{ppm}^{CDCl_3}$: 3.73, 4.00 (ABq, J=12 Hz, COC$\underline{H}_2$Cl), 5.0 (2H, s, OC$\underline{H}_2$Ph)

(e) A mixture of this product (6.9 g, 12.5 m mol) and sodium iodide (2.2 g, 12.5×1.2 mmol) in acetonitrile (50 ml) is heated at 70° C. over a period of an hour. The reaction mixture is concentrated in vacuo, and the residue is extracted with benzene. The benzene layer is washed with water, dried over anhydrous magnesium sulfate, and concentrated in vacuo to give 4-[N-iodoacetyl-4-chloro-2-(2-fluorobenzoyl)anilino]-1-benzyloxycarbonyl-piperidine (8.1 g) as an oil.

$^1$H NMR, $\delta_{ppm}^{CDCl_3}$: 3.33, 3.80 (ABq, J=10 Hz, COC$\underline{H}_2$I)

A mixture of above product (8.1 g), ammonium carbonate (14 g) and acetonitrile (20 ml) is heated in a sealed tube at 50° C. (bath temp.) over a period of 60 hours. After cooling, the reaction mixture is mixed with water and shaken with methylene chloride. The methylene chloride layer is washed with water, dried over anhydrous magnesium sulfate, and concentrated in vacuo. The residue is purified on Lobar ® column B, which is eluted with 10–20% ethyl acetate-methylene chloride mixture. Evaporation of the eluate affords 1-(1-benzyloxycarbonyl-4-piperidinyl)-7-chloro-1,3-dihydro-5-(2-fluorophenyl)-2H-1,4-benzodiazepin-2-one (2.89 g) as colorless powders. The total yield is 45%.

(f) A mixture of above product (2.89 g, 5.71 m mol), anisole (3.72 ml, 5.71×6 m mol), aluminum chloride (4.57 g, 5.7×6 m mol), methylene chloride (50 ml) and nitromethane (50 ml) is stirred at room temperature over a period of 20 hours. The reaction mixture is mixed with icy water and shaken with ether. The ether layer is shaken with dilute hydrochloric acid, and the aqueous layer is neutralized with 2N sodium hydroxide and extracted with ether. The ether layer is washed with ether, dried over anhydrous magnesium sulfate, and concentrated in vacuo. The residue (2.04 g) is recrystallized from methanol-ethyl acetate to give 7-chloro-1,3-dihydro-5-(2-fluorophenyl)-1-(4-piperidinyl)-2H-1,4-benzodiazepin-2-one (1.61 g) as crystals melting at 197°–199° C. (dec.). The hydrobromide, mp. 261–262 (dec.).

EXAMPLE 24–25

The reactions are performed as in Example 23, whereby the following products are obtained.

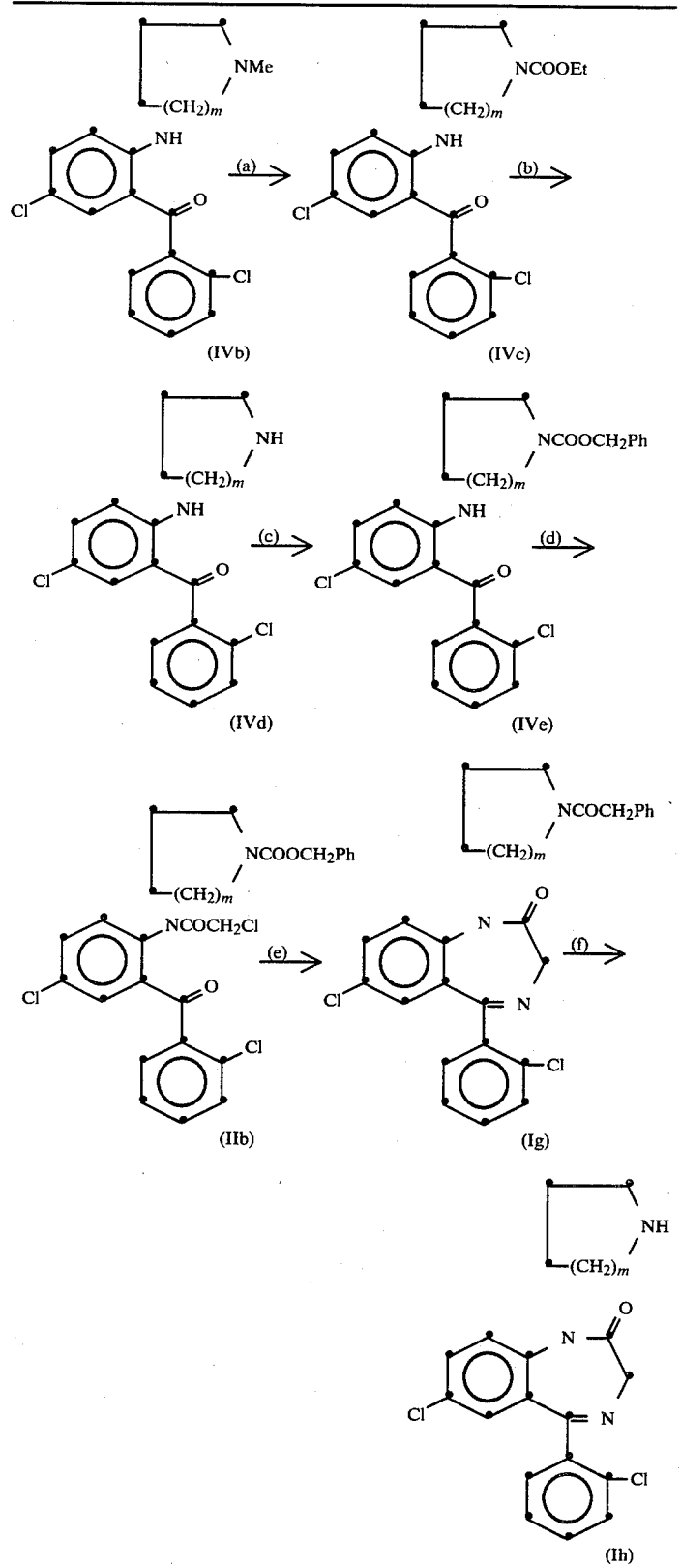
| | Example No. | | | |
|---|---|---|---|---|
| | 24* | | 25** | |
| Compound Symbol | mp(°C.)/IR(cm$^{-1}$) | Yield (%) | mp(°C.)/IR(cm$^{-1}$) | Yield (%) |

| | | | | |
|---|---|---|---|---|
| IVc | 3227(film) | quantitative | 3333(CHCl₃) | quantitative |
| | 1700 | | 1670 | |
| | 1630 | | | |
| IVd | 3300(film) | quantitative | 3228(film) | quantitative |
| | 1630 | | 1620 | |
| IVe | 3227(film) | quantitative | 3227(film) | 75 |
| | 1690 | | 1690 | (from IVb) |
| | 1620 | | 1620 | |
| IIb | 1680(film) | quantitative | 1690(film) | quantitative |
| Ig | 1670(CHCl₃) | 46 | 1680(film) | 53 |
| | | (from IVc) | | (from IVe) |
| Ih | 95–100(CHCl₃) | 97 | 133–136 | 34 |
| | 3686 | (from Ig) | | (from IVb) |
| | 1678 | | | |

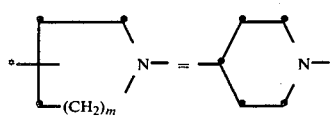

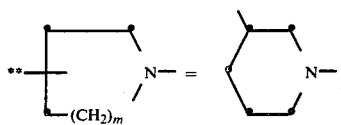

EXAMPLES 26–28

The reactions are performed according to Example 23 and partly to Example 5 (the part of the Gabriel Synthesis), whereby the following products are obtained.

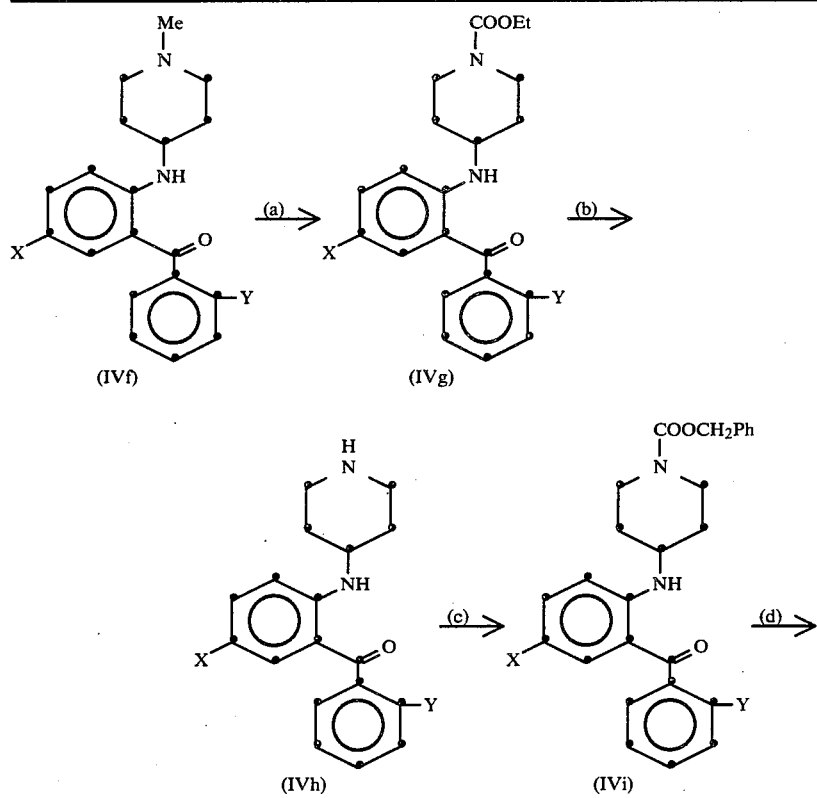

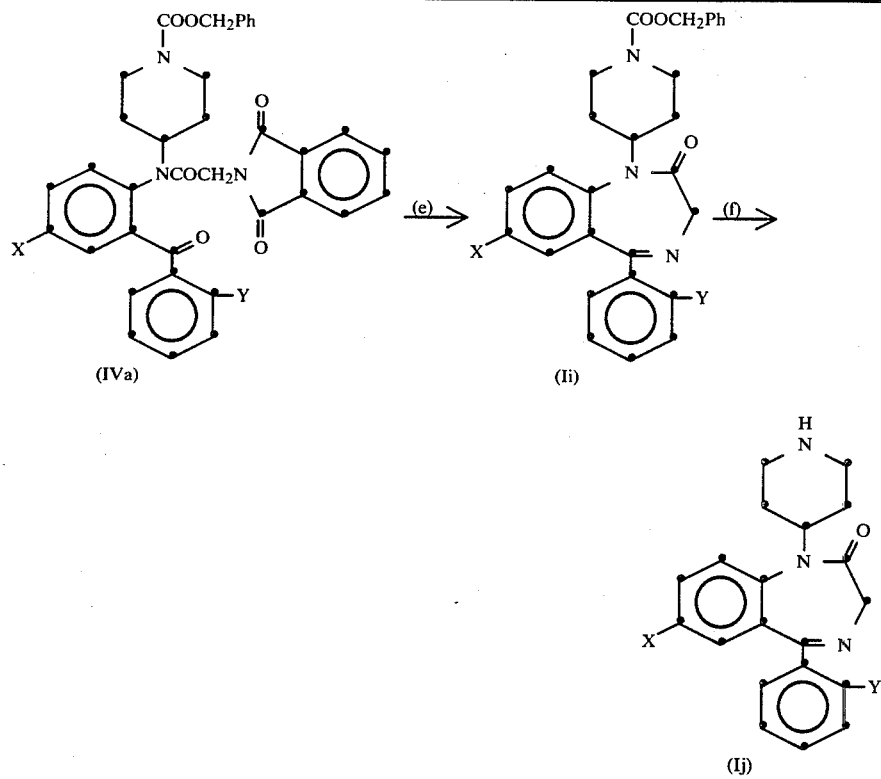

| Compound Symbol | Example No. 26* mp (°C.)/IR (cm$^{-1}$) | Yield (%) | 27 mp (°C.)/IR (cm$^{-1}$) | Yield (%) | 28* mp (°C.)/IR (cm$^{-1}$) | Yield (%) |
|---|---|---|---|---|---|---|
| IVg | 3227 (film) 1700 1620 | quantitative | 3227 (film) 1690 1620 | quantitative | 3300 (film) 1700 1620 | quantitative |
| IVh | 3300 (film) 1630 | quantitative | 3300 (film) 1620 | quantitative | 240–241 d. (HCl） | 97 (from IVf) |
| IVi | 3227 (film) 1698 1615 | 94 (from IVg) | 3227 (film) 1690 1620 | 98 (from IVg) | 3228 (film) 1690 1620 | quantitative |
| IIIa | 1780 (film) 1720 1670 | quantitative | 1770 (film) 1720 1660 | 94 (from IVi) | 148–149 | 82 (from IVi) |
| Ii | 1680 (film) | 80 (from IVi) | 1680 (film) | 89 (from IIIa) | 130–131 | 89 (from IIIa) |
| Ij | 281–283 d. (HBr) | 60 (from IVf) | 191–192**** | 75 (from IVf) | 166–167 | 71 (from IVf) |

*X = H, Y = H
**X = Cl, Y = H
***X = H, Y = F
****HBr H$_2$O, mp 262–265 (dec.).

EXAMPLE 29

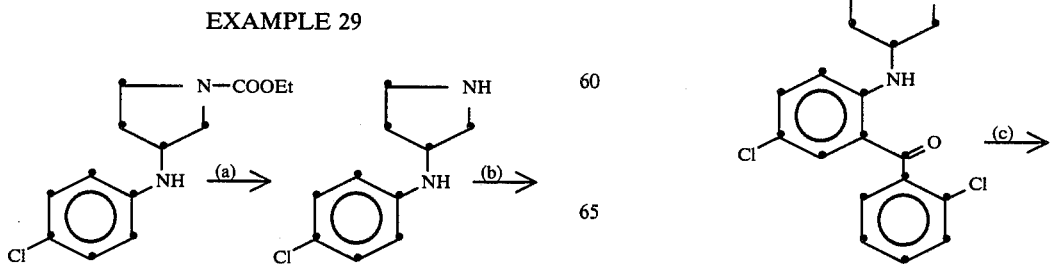

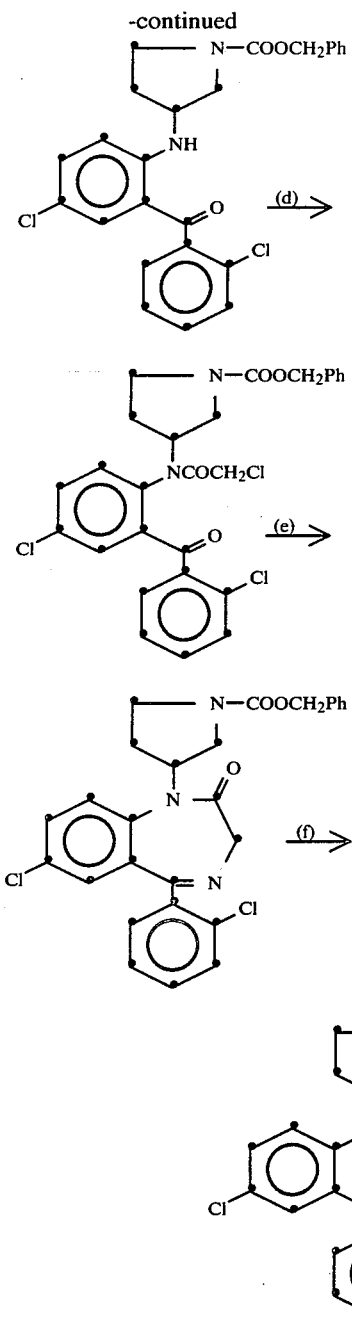

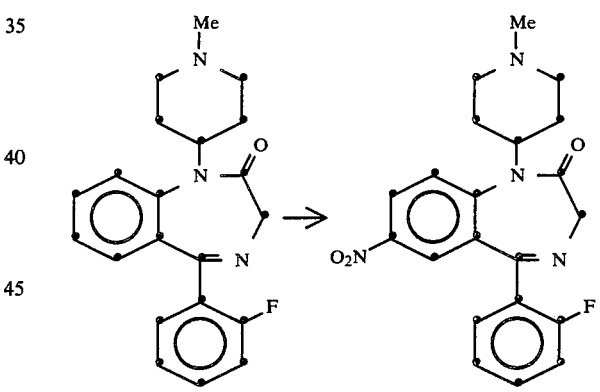

(a) A mixture of ethyl 3-(4-chloroanilino)pyrrolidine-1-carboxylate (7.20 g) and conc. hydrochloric acid (72 ml) is heated under reflux over a period of 20 hours. The reaction mixture is concentrated in vacuo, and the residue is crystallized from methanol-isopropanol to give 3-(4-chloroanilino)pyrrolidine dihydrochloride (6.99 g) as crystals melting at 120° to 143° C. The yield is 96%.

(b) To a suspension of above product (2.70 g, 10 m mol) and 2-chlorobenzonitrile (2.75 g, 20 m mol) in toluene (20 ml) is added a 1.23M solution of boron trichloride (20 ml), and the resultant mixture is heated under reflux over a period of 1 hour. The reaction mixture is concentrated in vacuo to remove the solvent, and the residue is heated at temperature of 150° C. over a period of 20 hours. After cooling, the residue is mixed with 2N hydrochloric acid (20 ml) and water (20 ml) and stirred under heating at 100° C. (bath temp.). The reaction mixture is shaken with methylene chloride, and the organic layer is washed with 2N hydrochloric acid and dilute ammoniac solution in order, dried over anhydrous magnesium sulfate, and concentrated in vacuo to give crude 3-[4-chloro-2-(2-chlorobenzoyl)anilino]pyrrolidine as an oil.

(c) As in the method of Example 19 (c), above product is treated with benzyl chlorocarbonate (1.4 ml), 1N aqueous sodium hydroxide (10 ml) and tetrahydrofuran (30 ml), and the resulting crude product is purified from Lobar ® column B, which is eluted with benzene-ethyl acetate (9:1 v/v) mixture. Evaporation of the eluate affords · 3-[4-chloro-2-(2-chlorobenzoyl)anilino]-1-benzyloxycarbonylpyrrolidine (1.78 g) as an oil. The yield is 38%.

IR, $\nu_{max}^{CHCl_3}$, 3400 (NH), 1690, 1625 (CO) cm$^{-1}$ $^1$H NMR, $\delta_{ppm}^{CDCl_3}$, 1.7–4.2 (m, aliphatic H), 5.12 (2H, s, OC$\underline{H_2}$Ph), 6.6–7.5 (m, aromatic H), 9.1 1H, d, J=6 Hz, N$\underline{H}$)

(d) to (f) The reactions are performed as in the method of Example 23, whereby the following products are obtained.

| Step | Product mp(°C.)/IR(cm$^{-1}$) | Yield (%) |
|---|---|---|
| d | 1690(CHCl$_3$) | 96 |
| e | 1690(CHCl$_3$) | 43 |
| f | 138–140(oxalate) | 73 |

EXAMPLE 30

To conc. sulfuric acid (10 ml) is added 1-(1-methyl-4-piperidinyl)-1,3-dihydro-5-(2-fluorophenyl)-2H-1,4-benzdiazepin-2-one (2.09 g; 5.95 m mol) under cooling at temperature of −8° C. A solution of potassium nitrate (571 mg, 5.95×0.95 m mol) in conc. sulfuric acid (5 ml) is dropwise added to the mixture at the same temperature, which is allowed to stand at −5° C. over a period of 6 hours and then at room temperature over a period of 15 hours. The reaction mixture is poured onto ice (200 g), neutralized with conc. aqueous ammoniac solution, and shaken with methylene chloride. The organic layer is washed with water, dried over anhydrous magnesium sulfate and concentrated in vacuo. The residue is chromatographed on a column of alumina, which is eluted with ethyl acetate. The eluate is concentrated in vacuo and the residue is crystallized from methylene chloride-ether to give 7-nitro-1-(1-methyl-4-piperidinyl)-1,3-dihydro-5-(2-fluorophenyl)-

2H-1,4-benzdiazepin-2-one (544 mg) as crystals melting at 199° to 201° C. (dec.). The yield is 23%.

EXAMPLE 31

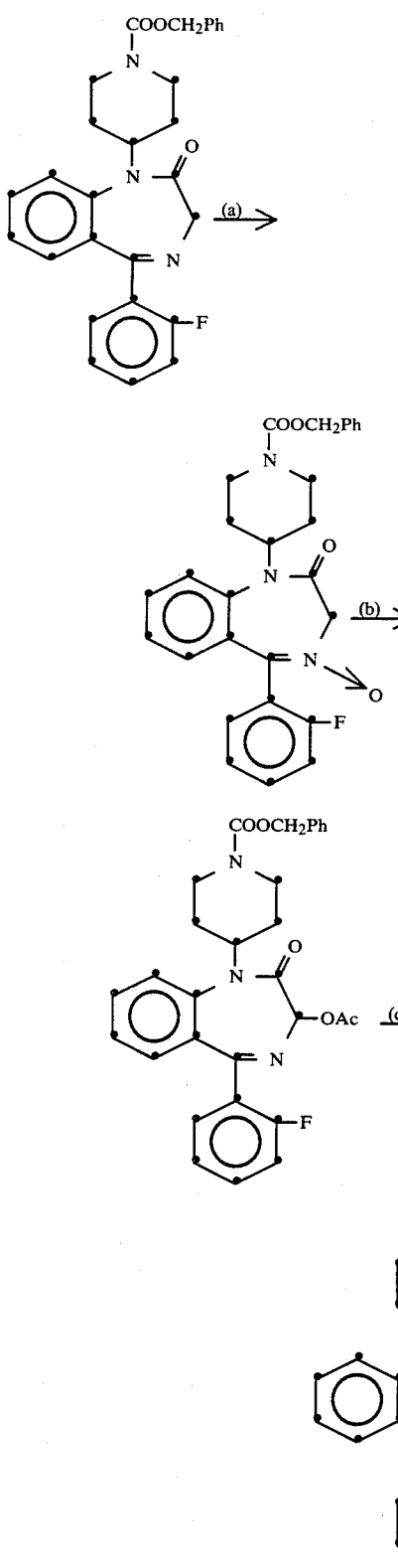

(a) To a solution of 1-(1-benzyloxycarbonyl-4-piperidinyl)-1,3-dihydro-5-(2-fluorophenyl)-2H-1,4-benzdiazepin-2-one (4.20 g, 8.91 m mol) in acetic acid (50 ml) is added 30% hydrogen peroxide (3.5 ml, 8.91×4.5 m mol), and the resultant mixture is heated at 65° C. over a period of 16 hours. After cooling, the reaction mixture is mixed with sodium hydrogen-sulfite (3.5 g) and concentrated in vacuo to about its quartered volume. The concentrated solution is neutralized with ice-aqueous ammoniac solution and extracted with methylene chloride. The organic layer is washed with water, dried over anhydrous magnesium sulfate, and concentrated in vacuo. The residue is chromatographed on a column of silica gel, which is eluted with ethyl acetate-benzene (1:1, v/v). The eluate is concentrated in vacuo to give the objective N-oxide (4.31 g) as an oil. The yield is 99%.

IR, $\nu_{max}^{CHCl_3}$: 1680 cm$^{-1}$ $^1$H NMR, $\delta_{ppm}^{CDCl_3}$: 4.6 (2H, s, COC$\underline{H}_2$N→O), 5.1 (2H, s, OC$\underline{H}_2$Ph)

(b) A mixture of above N-oxide (4.31 g) and acetic anhydride (25 ml) is heated at 140° C. (bath temp.) over a period of 1 hour, and the reaction mixture is concentrated in vacuo to remove the acetic anhydride. The residue is chromatographed on a column of silica gel, which is eluted with methylene chloride-ethyl acetate (5:1 v/v). The eluate is concentrated in vacuo to give 3-acetoxy compound (4.04 g) as an oil. The yield is 86%.

IR, $\nu_{max}^{CHCl_3}$: 1636, 1692 cm$^{-1}$ $^1$H NMR, $\delta_{ppm}^{CDCl_3}$: 2.26 (3H, s, OCOC$\underline{H}_3$), 5.10 (2H, s, OC$\underline{H}_2$Ph), 5.90 (1H, s, NC$\underline{H}$CO)
|
OAc (c) Above 3-acetoxy compound (4.04 g) is reacted in the system of aluminum chloride, anisole, nitromethane and methylene chloride as in the method of Example 23 (f). The product after extraction is crystallized from methylene chloride-ethyl acetate to give 1-(4-piperidinyl)-3-hydroxy-1,3-dihydro-5-(2-fluorophenyl)-2H-1,4-benzodiazepin-2-one (2.14 g) as crystals melting at 190° to 192° C. The yield is 79%.

EXAMPLE 32

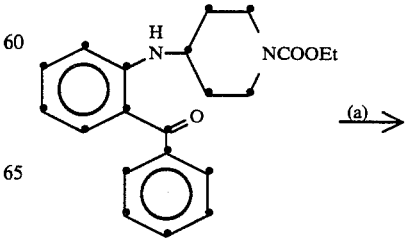

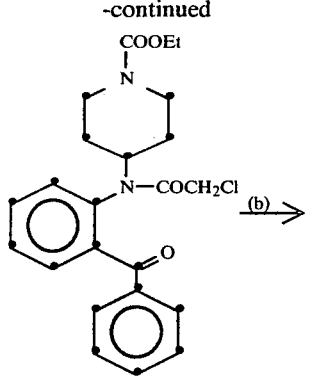

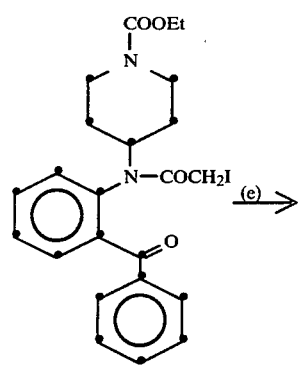

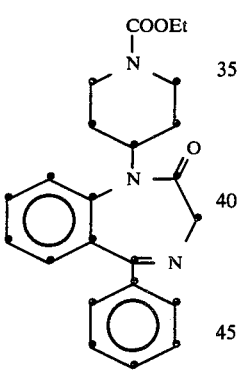

The reactions are performed as in the method of Example 23 (d) and (e). Thus ethyl 4-(2-benzoylanilino)-piperidine-1-carboxylate (2.56 g) is reacted successively with 2-chloro-acetyl chloride, sodium iodide and ammonium carbonate, whereby 1,3-dihydro-1-(1-ethoxycarbonyl-4-piperidinyl)-5-phenyl-2H-1,4-benzodiazepin-2-one (2.27 g) is obtained as a powder.

IR, $\nu_{max}^{CHCl_3}$: 1678 cm$^{-1}$ $^1$H NMR, $\delta_{ppm}^{CDCl_3}$: 1.23 (t, J=7 Hz, OCH$_2$C$\underline{H}_3$), 3.81, 4.79 (q, J=10 Hz, COC$\underline{H}_2$N)

The following intermediates are obtained.

(a) Chloroacetyl compound: an oil

IR, $\nu_{max}^{CHCl_3}$: 1665, 1690 cm$^{-1}$ (b) Iodoacetyl compound: used in Step (c) without further isolation.

EXAMPLE 33

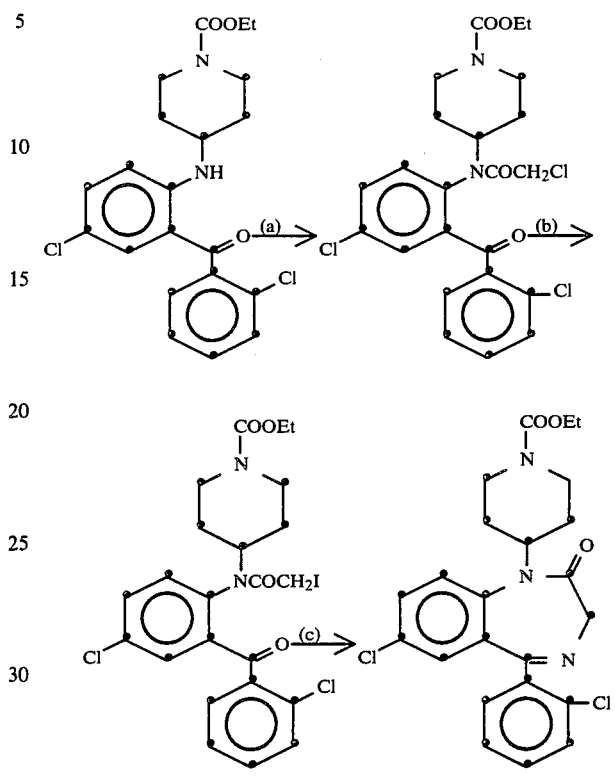

The reactions are performed as in the method of Example 23 (d) and (e), whereby the following products are obtained.

| Step | mp(°C.)/IR(cm$^{-1}$) | Yield (%) |
|---|---|---|
| a | 1680(CHCl$_3$) | quantitative |
| b | not isolated | — |
| c | 101–103 | 58 (overall yield) |

EXAMPLE 34

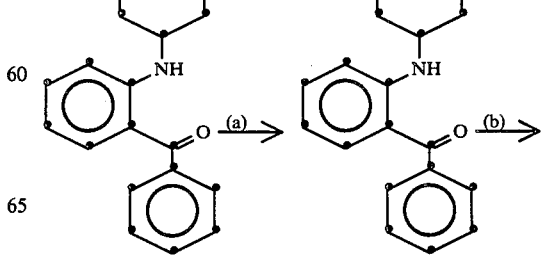

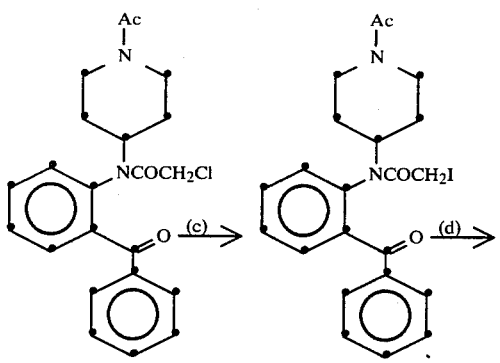

EXAMPLE 35

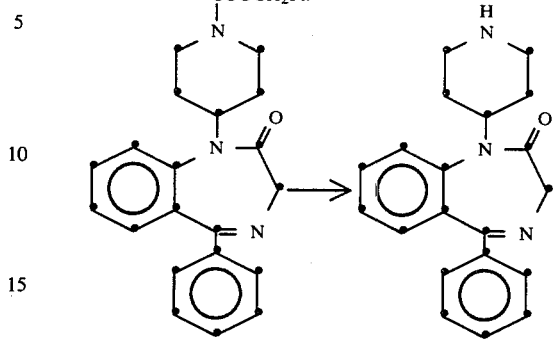

A mixture of 1-(1-benzyloxycarbonyl-4-peperidinyl)-1,3-dihydro-5-phenyl-2H-1,4-benzodiazepin-1-one (17.6 g) obtained in Example 26 (e) and trifluoroacetic acid (53 ml) is heated under reflux over a period of 2 hours, and the reaction mixture is concentrated in vacuo. The residue is mixed with ether (100 ml) and water (150 ml), and ether layer is separated. The aqueous layer is made alkaline with ammonia and extracted with methylene chloride. The methylene chloride layer is washed with water, dried over anhydrous magnesium sulfate, decolorized with active carbon, and concentrated in vacuo. The residue is dissolved in 90% ethanol (60 ml) and mixed with conc. hydrobromic acid (4.4 ml). The precipitated crystals are recrystallized from methanol to give 1-(4-piperidinyl)-1,3-dihydro-5-phenyl-2H-1,4-benzodiazepin-1-one hydrobromide (12.4 g) as crystals melting at 282° to 283° C. (dec.).

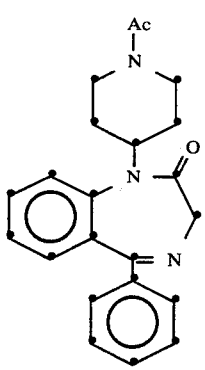

(a) A solution of 4-(2-benzoylanilino)piperidine (2.8 g) in acetic anhydride (5 ml) is allowed to stand at room temperature over a period of half an hour. The reaction mixture is mixed with ice and aqueous potassium carbonate, stirred over a period of half an hour and extracted with ether. The ether layer is washed with water and concentrated in vacuo. The residue is purified from Lobar ® column B, which is eluted with ethyl acetate. The eluate is concentrated in vacuo to give the N-acetate (3.0 g) as an oil.

IR, $v_{max}^{film}$: 3300–3400, 1680 cm$^{-1}$ (b)–(d) The N-acetate is treated as in the method of Example 23 (d) to (e), and the product is crystallized from methylene chloride-isopropanol to give 1,3-dihydro-1-(1-acetyl-4-piperidinyl)-5-phenyl-2H-1,4-benzodiazepin-2-one (2.1 g) as crystals melting at 208°–209° C.

Additionally the following intermediates are prepared.

(b) Chloroacetate: mp. 182°–184° C.

(c) Iodoacetate is used for Step (d) without further purification.

| Formulation | |
|---|---|
| Compound in Example 23 | 30 g |
| Wheat starch | 240 g |
| Lactose | 240 g |

These are admixed evenly. A desired amount of 5% gelatin solution is added to the mixture, which is dried and sieved. The resultant granules are admixed with talc (30 g) and subjected to a tableting machine to give 3000 tablets, each weighing 180 mg and containing 10 mg of the effective ingredient.

REFERENTIAL EXAMPLE 1

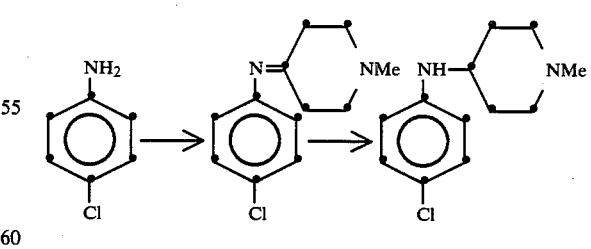

To a solution of 4-chloroaniline (4.59 g, 30×1.2 mmol) and 1-methyl-4-piperidone (3.39 g, 30 mmol) in benzene (12 ml) is added Molecular Sieve 4A (6 g), and the resultant mixture is heated under reflux over a period of 20 hours. After cooling, the reaction mixture is mixed with ether and filtered to remove the Molecular Sieve. The filtrate is concentrated in vacuo, and the residue is dissolved in 95% ethanol (50 ml). Sodium borohydride (0.6 g, 15 mmol) is added to the solution, which is stirred at room temperature over a period of 5 hours. The reaction mixture is mixed with water and the ethanol is evaporated therefrom. The aqueous residue is shaken with methylene chloride, and the methylene chloride layer is dried over anhydrous potassium carbonate and concentrated in vacuo. The residue is distilled to give crude product (5.89 g) b.p. 130°–150° C./1 mmHg. This substance is recrystallized from ether-petroleum ether to give 4-(4-chloroanilino)-1-methylpiperidine (5.25 g) as crystals melting at 91° to 92° C. The yield is 78%.

REFERENTIAL EXAMPLES 2–13

The reactions are performed as in the method of Example 1, whereby the following products are obtained.

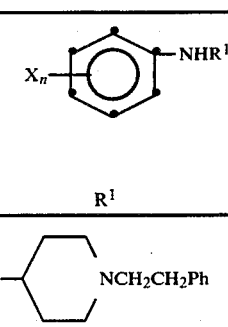

| Ref. Ex. No. | $X_n$ | $R^1$ | Yield (%) | mp (°C.)/ bp (°C./ mm Hg) |
|---|---|---|---|---|
| 2 | 4-Cl | -NCH₂CH₂Ph (cyclohexyl) | 74 | 83–84 |
| 3 | H | -NMe (cyclohexyl) | 78 | 82–83 |
| 4 | 3-Cl | " | 73 | 110–121 |
| 5 | 4-MeO | " | 82 | 180–145 |
| 6 | 4-(Me)₂N | " | 60 | 139–141 |
| 7 | 3-F | " | 71 | 104–106 |
| 8 | 3-CF₃ | " | 75 | 143–146/7 |
| 9 | 4-Br | " | 19 | 85–87 |
| 10 | 4-Me | " | 67 | 125–127 |
| 11 | 4-F | " | 79 | 92–93 |
| 12 | 3,4-Cl,Cl | " | 63 | 80–81 |
| 13 | 4-NO₂ | " | 56 | 153–155 |

REFERENTIAL EXAMPLE 14

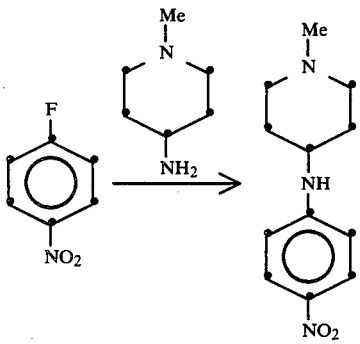

A mixture of 4-amino-1-methylpiperidine (4.82 g, 32.3 mmol) and 4-fluoronitrobenzene (4.56 g, 32.3 mmol) is heated at 100° C. on an oil bath over a period of 7 hours. After cooling, the reaction mixture is mixed with 2N hydrochloric acid (20 ml) and water (20 ml) and shaken with ether. The acidic layer is neutralized with conc. ammoniac solution and shaken with methylene chloride. The methylene chloride layer is washed with water, dried over anhydrous magnesium sulfate and concentrated in vacuo. The residue is crystallized from ether-petroleum ether to give 4-(4-nitroanilino)-1-methylpiperidine (4.27 g) as crystals melting at 153° to 155° C. The yield is 56%.

REFERENTIAL EXAMPLE 15

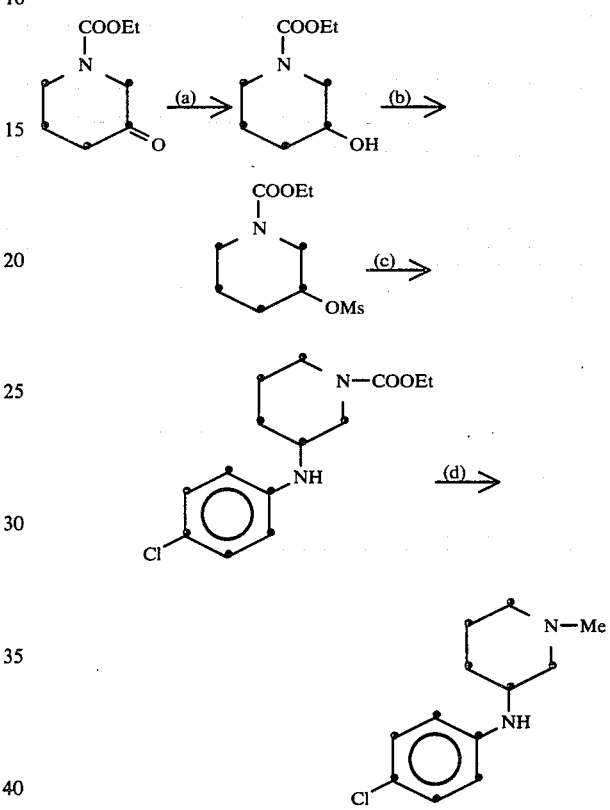

(a) To a solution of ethyl 3-oxo-1-piperidine-1-carboxylate (6 g. 35 mmol) in methanol (60 ml) is added sodium borohydrate (1.34 g, 35 mmol), and the resultant mixture is stirred at room temperature over a period of 1 hour. The reaction mixture is mixed with icy waters and shaken with methylene chloride. The organic layer is dried over anhydrous potassium carbonate and concentrated in vacuo to give ethyl 3-hydroxypiperidine-1-carboxylate (6.03 g) as an oil.

(b) To a solution of above product in pyridine (40 ml) is added mesyl chloride (3.2 ml, 35×1.2 mmol) under ice cooling, and the resultant mixture is allowed to stand at room temperature over a period of 20 hours. The reaction mixture is mixed with icy waters and shaken with ether. The organic layer is washed with water, dried over anhydrous sodium sulfate, and concentrated in vacuo to give ethyl 3-mesyloxypiperidine-1-carboxylate (8.7 g) as an oil.

IR, $\nu_{max}^{film}$: 1690 (N—COOEt), 1350, 1180 (OSO₂) cm$^{-1}$ $^1$H NMR $\delta_{ppm}^{CDCl_3}$: 3.05 (3H, s, OSO₂CH₃)

(c) A mixture of above product (8.7 g, 35 mmol) and 4-chloroaniline (13.3 g, 35×3 mmol) is heated at 160° C. over a period of half an hour. After cooling, the reaction mixture is mixed with icy waters and extracted with ether. The ether layer is washed with water, dried over anhydrous sodium sulfate, and concentrated in vacuo. The remaining 4-chloroaniline is distilled off under reduced pressure. The residue is purified on Lobar ® column B, which is eluted with chloroform:ethyl acetate (10:1 v/v). The eluate is concentrated to give ethyl 3-(4-chloroanilinopiperidine)-1-carboxylate (4.87 g) as an oil.

(d) To a suspension of lithium aluminum hydride (1.96 g, 17.2×3 mmol) in ether (50 ml) is dropwise added a solution of above product (4.87 g) in ether (20 ml) under ice cooling, and the resultant mixture is refluxed over a period of half an hour under stirring. After cooling, the reaction mixture is mixed with hydrous ether and 6N aqueous sodium hydroxide (4 ml) successively, and the insoluble material is filtered off. The ether layer is concentrated in vacuo to give 3-(4-chloroanilino)-1-methylpiperidine (3.91 g) as an oil. The yield is 100%.

IR, $\nu_{max}^{film}$: 3270 (NH) cm$^{-1}$ $^1$H NMR, $\delta_{ppm}^{CDCl_3}$: 1.2–4.0 (m, aliphatic H), 2.3 (s, NC$\underline{H}_3$), 6.4–7.3 (m, aromatic H)

REFERENTIAL EXAMPLE 16

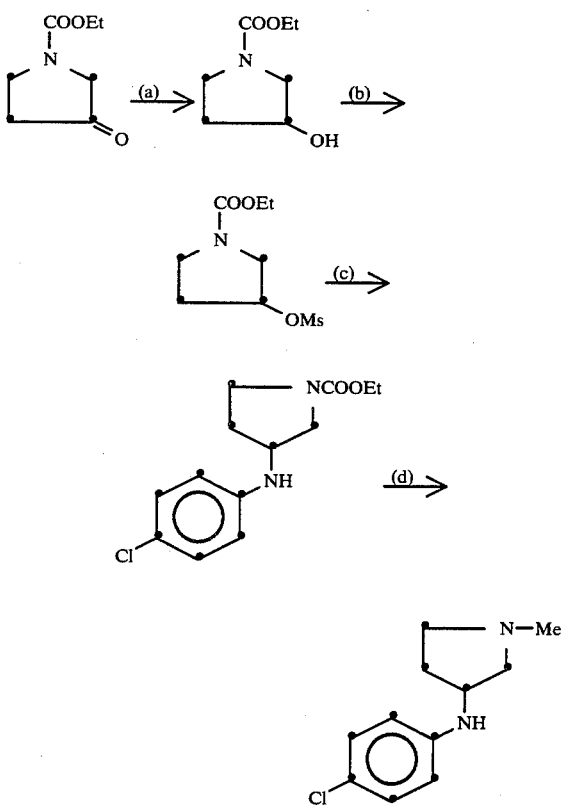

As in the method of Referential Example 15, the reactions are performed using ethyl 3-pyrrolidone-1-carboxylate, whereby the following products are prepared.

| Step | Yield (%) | mp(°C.)/IR(cm$^{-1}$) |
|------|-----------|------------------------|
| a | 94 | 3420, 1680 (film) |
| b | 84 | 1690, 1350, 1173 (film) |
| c | 83 | 50–51 |
| d | 87 | 91–94 |

REFERENTIAL EXAMPLE 17

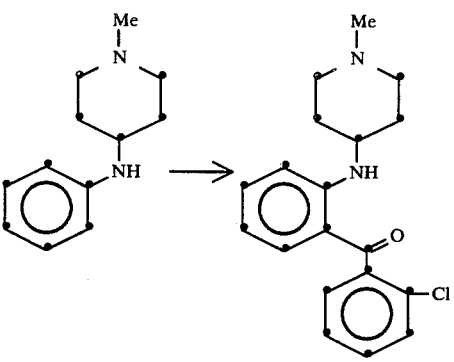

To a 2.03M solution of boron trichloride (25×1.2 mmol) in toluene (14.8 ml) is dropwise added a solution of 4-anilino-1-methylpiperidine (4.79 g, 25 mmol) in toluene (40 ml) under ice cooling and stirring, and the resultant mixture is refluxed under stirring over a period of 1 hour. The toluene is evaporated under atmospheric pressure from the reaction mixture, and the residue is mixed with 2-chlorobenzonitrile (6.88 g, 25×2 mmol) and heated at 150° C. (bath temp.) over a period of 15 hours under stirring. After cooling, the reaction mixture is mixed with 2N hydrochloric acid (15 ml) and water (30 ml) and heated at 100° C. under stirring over a period of 20 minutes. After cooling, the reaction mixture is washed with ether, and the aqueous layer is neutralized with conc. aqueous ammoniac solution and shaken with methylene chloride. The methylene chloride layer is dried over anhydrous potassium carbonate and concentrated in vacuo. The residue is chromatographed on a column of alumina, which is eluted with methylene chloride. The eluate is concentrated, and the residue is crystallized from ether-petroleum ether to give 4-[2-(2-chlorobenzoyl)anilino]-1-methylpiperidine (8.15 g) as crystals melting at 128° to 129° C. The yield is 99%.

REFERENTIAL EXAMPLES 18–36

The reactions are performed as in the method of Referential Example 17, whereby the following products are obtained.

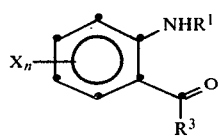
(IV)
| Ref. Ex. No. | $X_n$ | $R^1$ | $R^3$ | Yield (%) | mp (°C.)/ IR (cm$^{-1}$) |
|---|---|---|---|---|---|
| 18 | 4-Cl | ⟨cyclohexyl⟩-NCH$_2$CH$_2$Ph | Ph | 91 | 203–208(HCl) |
| 19 | H | ⟨cyclohexyl⟩-NMe | " | 99 | 193–203(2HBr) |
| 20 | " | " | —CH$_2$—(2-Br-Ph) | 95 | 3270(film) 1640 |
| 21 | 4-Cl | " | Ph | 98 | 3300(film) 1620 |
| 22 | " | " | 2-Cl—Ph | 92 | 101–102 |
| 23 | H | ⟨cyclohexyl⟩-NMe | 2-F—Ph | 97 | 98–100 |
| 24 | " | " | 4-F—Ph | 96 | 3280(film) 1610 |
| 25 | 4-Cl | " | 2-F—Ph | 99 | 3280(film) 1610 |
| 26 | 3-CF$_3$ | " | " | 48 | 3290(film) 1030 |
| 27 | 3-Cl | " | " | 100 | 3190(film) 1610 |
| 28 | 3-F | " | " | 67 | 118–120 |
| 29 | 4-Br | " | " | 97 | 3280(film) 1620 |
| 30 | 4-Me | " | " | 95 | 3280(film) 1620 |
| 31 | 4-F | " | " | 100 | 3290(CHCl$_3$) 1630 |
| 32 | 3,4-Cl,Cl | " | " | 86 | 3280(film) 1620 |
| 33 | 4-Cl | ⟨cyclohexyl⟩-NMe | 2-Cl—Ph | 93 | 3270(film) 1620 |
| 34 | " | ⟨cyclohexyl⟩-NMe | " | 95 | 205–209(d) |

REFERENTIAL EXAMPLE 35

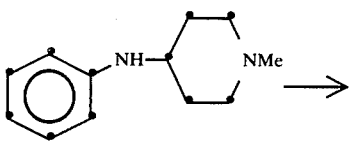

↓

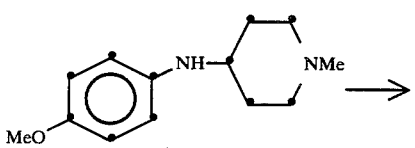

To a 2.03M solution of boron trichloride (20×1.2 mmol) in dichloroethane (11.8 ml) is dropwise added a solution of 4-anilino-1-methylpiperidine (3.81 g, 20 mmol) in dichloroethane (38 ml), and acetonitrile (2.1 ml, 20×1.2 mmol) is added to the mixture, which is heated under reflux over a period of 20 hours. After cooling, the reaction mixture is mixed with 2N hydrochloric acid (15 ml) and water (30 ml) and stirred at 100° C. over a period of 20 minutes. After cooling, the reaction mixture is mixed with conc. aqueous ammoniac solution and separated. The organic layer is washed with water, dried over anhydrous potassium carbonate and concentrated in vacuo to give 4-(2-acetylanilino)-1-methylpiperidine (4.41 g) as an oil. The yield is 95%.

IR, $\nu_{max}^{film}$: 3260 (NH), 1630 (CO) cm$^{-1}$ $^1$H NMR, $\delta_{ppm}^{CDCl_3}$: 1.5–3.7 (m, aliphatic H), 2.3 (s, NC$\underline{H}_3$), 2.55 (s, COC$\underline{H}_3$), 6.4–7.8 (m, aromatic H), 9.0 (1H, d, J=6 Hz, N$\underline{H}$)

REFERENTIAL EXAMPLE 36

The reaction is performed as in the method of Referential Example 35, whereby the following product is obtained.

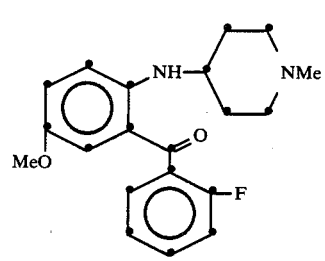

mp. 117°–118° C. yield 56%.

What we claim is:

1. A compound of the formula:

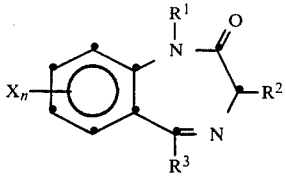

in which
R$^1$ is pyrrolidinyl or piperidinyl each optionally substituted by phenyl-C$_{1-3}$ alkyl, C$_{1-5}$ alkanoyl, or C$_{2-5}$ alkoxycarbonyl,
R$^2$ is hydrogen, hydroxy, or acetoxy,
R$^3$ is C$_{1-3}$ alkyl, phenyl-C$_{1-3}$ alkyl, or phenyl optionally substituted by one or two halogens,
X is hydrogen, halogen, C$_{1-3}$ alkyl, C$_{1-3}$ alkoxy, nitro, trifluoromethyl, or di-C$_{1-3}$ alkyl-amino, and
n is 1 or 2
or pharmaceutically acceptable acid addition salts thereof.

2. A compound according to claim 1, in which R$^2$ is hydrogen or hydroxy.

3. A compound according to claim 1, in which R$^3$ is phenyl optionally substituted by halogen.

4. A compound according to claim 1, in which X is halogen or nitro.

5. A compound according to claim 1, in which R$^2$ is hydrogen.

6. A compound according to claim 1, in which R$^3$ is 2-halo-phenyl.

7. A compound according to claim 1, in which X is 7-halogen.

8. A compound of the formula:

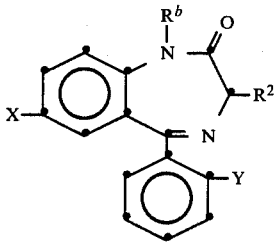

in which R$^b$ is 3-pyrrolidinyl or 4-piperidinyl each optionally substituted by phenyl-C$_{1-3}$ alkyl, C$_{1-5}$ alkanoyl, or C$_{2-5}$ alkoxycarbonyl, R$^2$ is hydrogen or hydroxy, and X and Y each is hydrogen or halogen.

9. A compound according to claim 1, namely 7-chloro-1,3-dihydro-1-(4-piperidinyl)-5-(2-fluorophenyl)-2H-1,4-benzodiazepin-2-one.

10. A compound according to claim 1, namely 7-chloro-1,3-dihydro-1-(4-piperidinyl)-5-phenyl-2H-1,4-benzodiazepin-2-one.

11. A compound according to claim 1, namely 7-chloro-1,3-dihydro-1-(1-methyl-4-piperidinyl)-5-phenyl-2H-1,4-benzodiazepin-2-one.

12. A compound according to claim 1, namely 1,3-dihydro-1-(4-piperidinyl)-5-phenyl-2H-1,4-benzodiazepin-2-one.

13. A compound according to claim 1, namely 7-chloro-1,3-dihydro-1-(4-piperidinyl)-5-(2-chlorophenyl)-2H-1,4-benzodiazepin-2-one.

14. A pharmaceutical composition comprising a psychotropically effective amount of a compound according to claim 1 and a pharmaceutically acceptable carrier, diluent, and/or excipient.

15. A method of treating a patient suffering from psychotic disorders which comprises administering a pharmaceutical composition according to claim 14 to the patient.

* * * * *